US009697980B2

(12) United States Patent
Ogura et al.

(10) Patent No.: US 9,697,980 B2
(45) Date of Patent: Jul. 4, 2017

(54) RADIATION GENERATING TUBE AND RADIATION GENERATING APPARATUS INCLUDING RADIATION GENERATION TUBE

(71) Applicant: CANON KABUSHIKI KAISHA, Tokyo (JP)

(72) Inventors: Takao Ogura, Yokohama (JP); Ichiro Nomura, Atsugi (JP); Kazuyuki Ueda, Tokyo (JP); Takashi Shiozawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 196 days.

(21) Appl. No.: 14/010,161

(22) Filed: Aug. 26, 2013

(65) Prior Publication Data
US 2014/0064447 A1   Mar. 6, 2014

(30) Foreign Application Priority Data

Aug. 28, 2012   (JP) ................................ 2012-187615

(51) Int. Cl.
*H01J 35/16*   (2006.01)
*A61B 6/06*   (2006.01)
(Continued)

(52) U.S. Cl.
CPC ............... *H01J 35/16* (2013.01); *A61B 6/06* (2013.01); *A61B 6/40* (2013.01); *A61B 6/08* (2013.01);
(Continued)

(58) Field of Classification Search
CPC ............... H01J 35/16; H01J 2235/081; H01J 2235/086; H01J 2235/087;
(Continued)

(56) References Cited

U.S. PATENT DOCUMENTS 4,882,741 A * 11/1989 Brown .......................... 378/152
2009/0010393 A1* 1/2009 Klinkowstein et al. ...... 378/140
(Continued)

FOREIGN PATENT DOCUMENTS

JP   S61-100406 U   6/1986
JP   H06-217973 A   8/1994
(Continued)

OTHER PUBLICATIONS

Jensen et al.,"Improvements in Low Power, End-Window, Transmission-Target X-Ray Tubes", Advances in X-Ray Analysis, 2004, pp. 64-69, vol. 47.

*Primary Examiner* — Glen Kao
(74) *Attorney, Agent, or Firm* — Canon USA Inc., IP Division

(57) ABSTRACT

A radiation generating apparatus includes a radiation generation tube including an electron emitting source having an electron emitting member, a transmission type target, a tubular backward shielding member having an electron passing hole facing the target layer at one end, located at the electron emitting source side of the transmission type target, and connected to the periphery of the base member. The radiation generating apparatus further includes a collimator having an opening for defining an angle for extracting the radiation at the opposite side of the electron emitting source side of the transmission type target, and an adjusting device connected to the collimator, and configured to vary an opening diameter of the opening, wherein the target layer has a portion separated from a connection portion of the base member and the backward shielding member at the periphery.

19 Claims, 7 Drawing Sheets

(51) Int. Cl.
*A61B 6/00* (2006.01)
*A61B 6/08* (2006.01)
*G21K 1/02* (2006.01)

(52) U.S. Cl.
CPC .......... *G21K 1/02* (2013.01); *H01J 2235/081* (2013.01); *H01J 2235/086* (2013.01); *H01J 2235/087* (2013.01); *H01J 2235/168* (2013.01)

(58) Field of Classification Search
CPC ........ H01J 2235/168; A61B 6/06; A61B 6/08; A61B 6/40; G21K 1/02
See application file for complete search history.

(56) References Cited

U.S. PATENT DOCUMENTS

2009/0190714 A1* 7/2009 Partain .......................... 378/19
2010/0054408 A1* 3/2010 Echner ......................... 378/65
2011/0255664 A1* 10/2011 Ueda et al. .................... 378/62

FOREIGN PATENT DOCUMENTS

| JP | 2002-352754 A | 12/2002 |
| JP | 2009-100948 A | 5/2009 |
| JP | 2009-219654 A | 10/2009 |
| JP | 2009545840 A | 12/2009 |
| JP | 2010115270 A | 5/2010 |
| JP | 2012-124098 A | 6/2012 |
| JP | 2012-147978 A | 8/2012 |

* cited by examiner

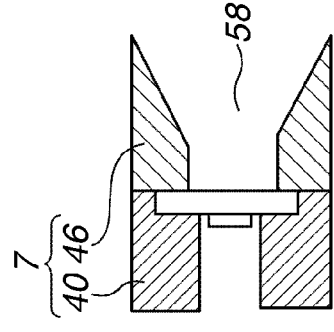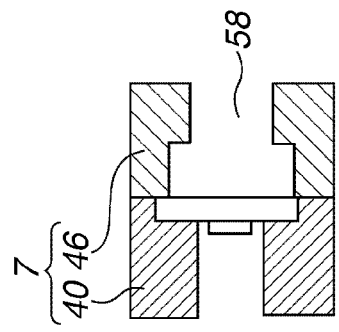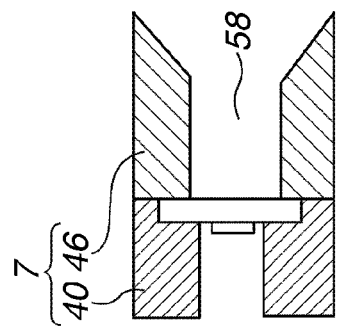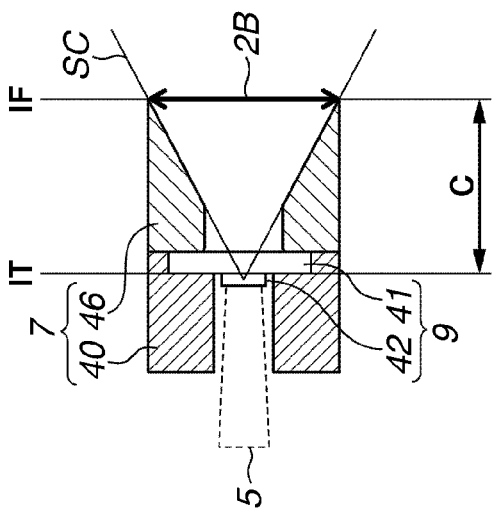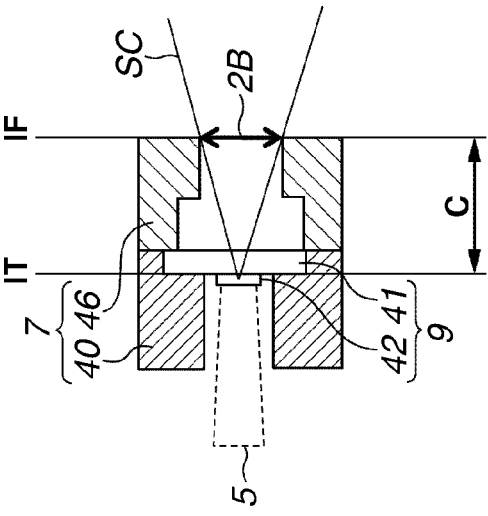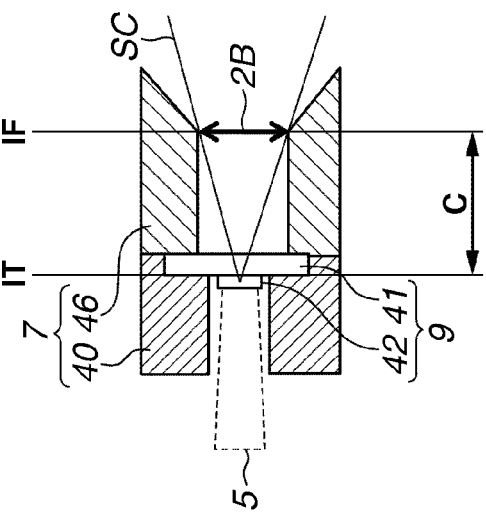

FIG.5A
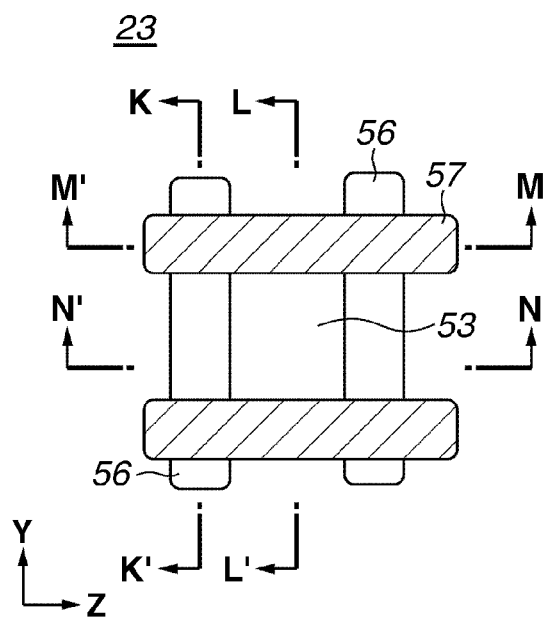
FIG.5B  FIG.5C
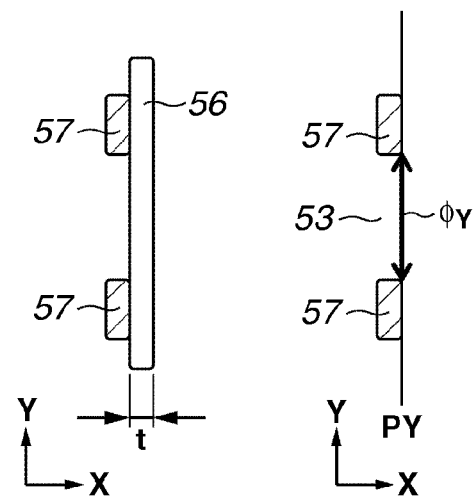
FIG.5D
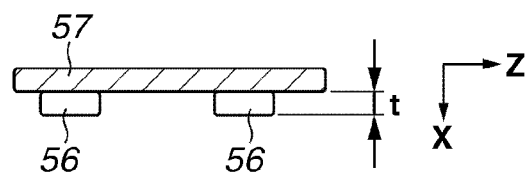
FIG.5E
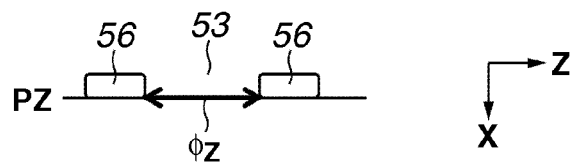

RADIATION GENERATING TUBE AND RADIATION GENERATING APPARATUS INCLUDING RADIATION GENERATION TUBE

BACKGROUND OF THE INVENTION

Field of the Invention

The present invention relates to a radiation generating tube, and a radiation generating apparatus including the radiation generating tube.

Description of the Related Art

Needs for small and lightweight medical modality with portability have been increasing with changing of social conditions such as improvement in the home medical care system and expansion of the range of treatment in emergency medical system. To respond to these needs, with developing of analysis diagnostic techniques in the medical field, various medical modalities have been developed. Radiation imaging apparatuses having a radiation source are, due to the sizes of the apparatuses, mainly fixed and installed in hospitals and medical testing facilities. Such radiation generating apparatuses having the radiation source are also required to be reduced in size and weight to use them as modalities applicable to home medical care and emergency medical care in disasters, accidents, and the like.

Factors determining the weight and size of radiation generating apparatuses include "radiation generation efficiency" and "shielding member". The "radiation generation efficiency" means a radiation output intensity to kinetic energy of incident electrons, and a low conversion efficiency of the radiation generation efficiency has been a problem in size reduction and weight reduction. By increasing the radiation generation efficiency, size reduction and weight reduction of a drive circuit and a radiation member constituting a large part of a radiation generating apparatus in the volume and mass can be achieved.

The "shielding member" means heavy metallic parts disposed around the whole container of a radiation generation apparatus to prevent emission of radiation except for emission in a direction of necessary radiation flux. The shielding member is disposed to surround a radiation source, and therefore it increases the volume of the radiation generating member, which in turn increases the weight and size of the radiation generating apparatus.

As a method for increasing the "radiation generation efficiency", a method of replacing a target from a reflection type target to a transmission type target has been proposed. Japanese Unexamined Patent Application Publication (Translation of PCT Application) No. 2009-545840 discusses a technique to increase "radiation generation efficiency" by a factor of 1.5 by replacing a conventional rotating-anode-type reflection-type target with a rotating-anode-type transmission-type target, and, in the same rotation conditions, to increase a peak of an electron injection amount by a factor of 1.3.

Further, in radiation generating apparatuses used for living body diagnosis in the medical field, a technique of providing, between the subject and a radiation source, a variable opening type collimator for determining a predetermined exposure range depending on a size of a specimen or a subject is known. In such a radiation generating apparatus, radiation emission to areas other than a predetermined observation field is not useful, and the variable opening type collimator is used to limit the amount of unnecessary exposure to the specimen or subject.

Japanese Unexamined Patent Application Publication (Translation of PCT Application) No. 2009-545840 discusses a radiation generating apparatus having an electron source and a transmission type target separately arranged, in which, at the rear side of the transmission type target, that is, at the side opposite to the electron source of the transmission type target, a collimator for limiting an emission angle of the radiation generated at the transmission type target is provided.

Further, Japanese Patent Application Laid-Open No. 2010-115270 discusses a multiple radiation generating apparatus having a plurality of transmission type targets arranged in one-dimensional array or in two-dimensional array. In the multiple radiation generating apparatus disclosed in Japanese Patent Application Laid-Open No. 2010-115270, at the rear side of each of the radiation generating apparatuses, a forward shielding member for limiting an emission angle of the radiation generated at the transmission type target, and a variable opening type collimator for changing the emission direction and the emission angle of the generated radiation are arranged.

Further, an anode assembly having a silver target layer, a window material made of beryllium for supporting the target layer, and a window supporting member made of NiCuFe alloy is discussed in an article published by International Centre for Diffraction Data 2004, Advances in X-ray Analysis, Volume 47, entitled "Improvements in low power, end-window, transmission-target X-ray tubes". Further, the article published by International Centre for Diffraction Data 2004, Advances in X-ray Analysis, Volume 47 entitled "Improvements in low power, end-window, transmission-target X-ray tubes" discusses that radiation due to the window supporting member, the radiation having quality different from that of the radiation due to the target layer contaminates the radiation spectrum. Accordingly, a collimator is disposed between a camera and a radiation generation tube to separate and detect the radiation due to the window supporting member and the radiation due to the target layer.

In the known radiation generating apparatuses having the reflection type target, by replacing the reflection type target with the transmission type target, in addition to the above-described increase in "radiation generation efficiency", an advantage of "low output angle dependence in focal diameter" can be achieved.

Japanese Unexamined Patent Application Publication (Translation of PCT Application) No. 2009-545840 discusses advantages of the transmission type target as compared to the reflection type target, that is, to "reduce apparent output angle dependence in focal diameter" on the target observed from the target side, and to "increase output angle" of the radiation flux. Japanese Unexamined Patent Application Publication (Translation of PCT Application) No. 2009-545840 further discusses a technique to cut a part of radiation flux having a large emission angle emitted from the transmission type target by the collimator disposed between the object and the radiation target.

As described above, an exposure range corresponding to an intended use can be provided by limiting the emission angle of the radiation flux generated from the radiation source having the transmission type target using the collimator. However, the emitted radiation flux may include radiation (referred to as off-focal radiation) generated at spots other than the focal spot of the electron beam formed on the target. The off-focal radiation is generated by irradiating with electrons a member disposed at a place other than the focal spot, the member including a heavy element. Such off-focal radiation decreases the resolution of the radiation diagnostic image, and consequently, the off-focal radiation is to be reduced as much as possible while maintaining the intensity of the radiation within the focal spot.

Hereinafter, with reference to FIGS. 7A to 7D, factors of the off-focal radiation generation will be described. FIGS. 7B to 7D are schematic views (upper diagram in each drawing) illustrating generation processes of off-focal radiation generated when an electron beam 5 is emitted toward a target 9 having a target layer 42 on one entire surface of a base member 41 for each track of backscattering reflected electrons, and distribution diagrams (lower diagram in each drawing) illustrating off-focal radiation generation distributions.

With reference to FIGS. 7A and 7B, off-focal radiation due to re-entering reflected electrons to target (hereinafter, referred to as off-focal radiation due to re-entering) will be described.

In FIG. 7A, the electron beam 5 directly enters the target layer 42 so that a focal diameter 30 is formed on the target layer 42 of the target 9. From the range of the focal diameter 30, a part of the directly entered electron beam 5 scatters backward, and a part of the backscattering electrons re-enters the target layer 42 due to a potential gradient existing between an electron emitting source (not illustrated) and the target layer 42, and becomes re-entering electrons 31.

The energy distribution of the backscattering electrons from the target layer 42 includes elastic scattering electrons. The elastic scattering electrons, according to the law of conservation of energy, re-enters the target layer 42 with the same energy as the electron beam 5 directly entering the target layer 42, and generates off-focal radiation 32 at the outside of radiation 51 within focal spot. In FIG. 7A, to facilitate the understanding, the radiation 51 within focal spot and the off-focal radiation 32 are expressed to emit radiation toward the front of the target 9 with emission angles. In actuality, however, although the radiation 51 and the radiation 32 have individual emission angle distributions respectively, the radiation 51 and the radiation 32 are emitted in all directions from the target layer 42.

FIG. 7B illustrates a generation mechanism of the off-focal radiation due to re-entering radiation and a distribution of the radiation generation area. In FIG. 7B, $\eta(y)$ is a radiation intensity distribution due to re-entering reflected electrons to the target, and y shows a relative position of the target layer 42 in the in-plane direction. The radiation intensity distribution $\eta(y)$ of the off-focal radiation due to re-entering radiation exceeds the focal diameter 30 due to direct incident electrons and is shown as a broad distribution 55. As described above, the off-focal radiation due to re-entering reflected electrons generates, at the outside of the focal spot due to the direct incident, off-focal radiation having a diameter larger than the focal diameter 30.

With reference to FIG. 7C, off-focal radiation due to target incidence reflected electrons to backward shielding member (hereinafter, referred to as off-focal radiation due to the backward shielding member) will be described. FIG. 7C illustrates a generation mechanism of the off-focal radiation due to the backward shielding member and a distribution of the radiation generation area.

FIG. 7C is similar to FIGS. 7A and 7B in that the electron beam 5 directly enters the target layer 42 to form the focal diameter 30 on the target layer 42 of the target 9. FIG. 7C differs from FIGS. 7A and 7B in that the arrangement includes a backward shielding member 40 located in a rearward position with respect to the target 9, that is, located at the side of the electron emitting source (not illustrated) as a peripheral structure of the target 9.

In FIG. 7C, from the range of the focal diameter 30 due to the directly entering electron beam 5, backscattering reflected electrons 33 are generated, and a part of the reflected electrons 33 enters the backward shielding member 40. The backward shielding member 40 is a member containing a heavy metal, and generates radiation in response to reception of the entering reflected electrons 33. A part of the generated radiation is emitted toward the front of the target 9. As a result, as illustrated in the lower diagram of FIG. 7C, an off-focal radiation intensity distribution $\xi(y)$ is generated to have peaks at positions corresponding to the inner wall of the backward shielding member 40.

In FIG. 7C, $\xi(y)$ is a radiation intensity distribution due to the target incidence reflected electrons to the backward shielding member, and y shows a relative position of the target layer 42 in the in-plane direction.

With reference to FIG. 7D, off-focal radiation due to target incidence of re-entering reflected electrons of target reflected electrons to the backward shielding member (hereinafter, referred to as off-focal radiation due to re-entering reflected electrons) will be described. FIG. 7D illustrates a generation mechanism of the off-focal radiation due to re-entering reflected electrons and a distribution of the radiation generation area.

FIG. 7D is similar to FIG. 7C in that the electron beam 5 directly enters the target layer 42 to form the focal diameter 30 on the target layer 42 of the target 9, and the arrangement includes the backward shielding member 40 located in the rearward position with respect to the target 9 as a peripheral structure of the target 9.

In FIG. 7D, from the range of the focal diameter 30 due to the directly entering electron beam 5, backscattering reflected electrons 33 are generated, and a part of the reflected electrons 33 enters the backward shielding member 40. Similar to the generation mechanism of the off-focal radiation due to backward shielding member, the backward shielding member 40 generates radiation in response to reception of the entering reflected electrons 33 and a part of the entered electrons elastically scatters. A part of the elastically scattering electrons (re-reflected electrons 34) re-enters the target layer 42. As a result, as illustrated in the lower diagram of FIG. 7D, a broad off-focal radiation intensity distribution $\zeta(y)$ is generated to have peaks at positions corresponding to the inside of the inner wall of the backward shielding member 40.

In FIG. 7D, $\zeta(y)$ is a radiation intensity distribution due to the target incidence of the re-reflected electrons of the target reflected electrons to the backward shielding member 40, and y is a relative position of the target layer 42 in the in-plane direction.

The individual radiation intensity distributions $\eta(y)$, $\xi(y)$, and $\zeta(y)$ are observed by a radiation detector (not illustrated) disposed in front of the target 9, that is, at the side of the base member 41 of the target 9.

The off-focal radiation to be solved in the present invention is generated due to at least one of the three types of off-focal radiation generated depending on a scattering angle $\theta bs$ of the backscattering electrons of the target layer 42, an arrangement, and a material of the backward shielding member. The backscattering electrons have a continuous scattering angle probability distribution in the range of 0 degrees$\leq \theta bs < 90$ degrees, and consequently, normally, the three types of off-focal radiation are generated at the same time.

As described above, at least one embodiment of the present invention is directed to a radiation generating apparatus capable of reducing each of the off-focal radiation due to the three factors while maintaining the advantages of high power performance, and the small and lightweight properties of the radiation generating apparatus having the transmission target. Further, the present invention is directed to providing a radiation imaging apparatus having a radiation generating apparatus reducing the off-focal radiation and capable of obtaining a high-resolution shot image.

In the description of the above-described "off-focal radiation due to re-entering radiation" with reference to FIGS. 7A and 7B, to facilitate understanding, the backward shielding member 40 is not illustrated, however, in a target peripheral structure having the tubular backward shielding member 40, similarly to FIGS. 7C and 7D, the off-focal radiation due to re-entering radiation is generated.

SUMMARY OF THE INVENTION

According to an aspect of the present invention, a radiation generating apparatus include a radiation generation tube including an electron emitting source having an electron emitting member, a target having a target layer receiving emission of an electron beam emitted from the electron emitting member and generating radiation, and a base member supporting the target layer and transmitting the radiation, in which the electron emitting source and the target layer are disposed to face each other, a tubular backward shielding member having an electron passing hole facing the target layer at one end, located at the electron emitting source side of the target, and connected to the periphery of the base member. The radiation generating apparatus further includes a collimator having an opening for defining an angle for extracting the radiation at the opposite side of the electron emitting source side of the target, and an adjusting device connected to the collimator, and configured to vary an opening diameter of the opening, wherein the target layer has a portion separated from a connection portion of the base member and the backward shielding member at the periphery.

Further features of the present invention will become apparent from the following detailed description of exemplary embodiments with reference to the attached drawings.

BRIEF DESCRIPTION OF THE DRAWINGS

FIGS. 4A to 4C illustrate modifications of a forward shielding member according to an exemplary embodiment.

FIGS. 4D to 4F illustrate examples of outgoing opening diameter definitions of the forward shielding member.

FIG. 5A is a plan view illustrating a collimator according an exemplary embodiment. FIGS. 5B to 5E are cross-sectional views of the collimator.

FIG. 7B illustrates a generation mechanism of off-focal radiation due to re-entering radiation. FIG. 7C illustrates a generation mechanism of off-focal radiation due to backward shielding member. FIG. 7D illustrates a generation mechanism of off-focal radiation due to re-entering reflected electrons.

DESCRIPTION OF THE EMBODIMENTS

Figure 1A:
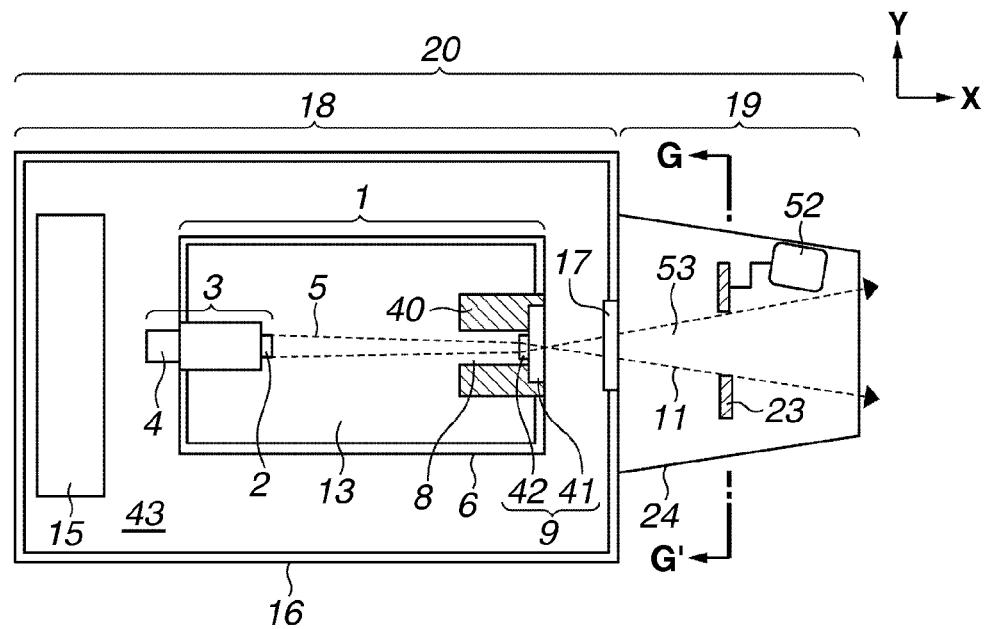
FIG. 1A is an overall view illustrating a radiation generating apparatus according to an exemplary embodiment of the present invention.
Figure 1B:
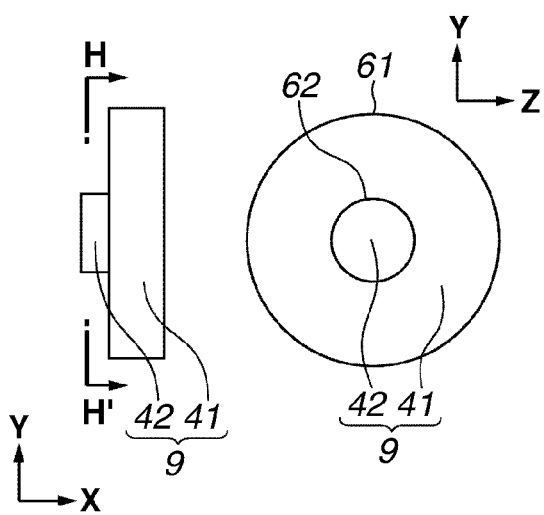
FIG. 1B illustrates a structure of a target according to an exemplary embodiment of the present invention.
Figure 1C:
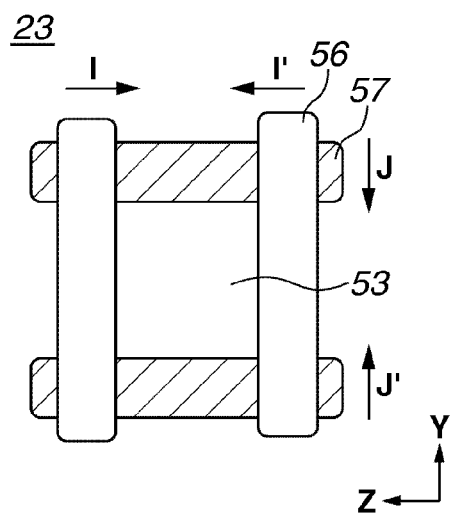
FIG. 1C illustrates a structure of a collimator according to an exemplary embodiment of the present invention.

With reference to FIGS. 1A to 1C, a basic structure of a radiation generating apparatus according to an exemplary embodiment of the present invention will be described. FIG. 1A is an overall view illustrating a radiation generating apparatus according to the present exemplary embodiment. Further, FIG. 1B illustrates a structure of a target applicable to the radiation generating apparatus according to the present exemplary embodiment. Further, FIG. 1C illustrates a collimator applicable to the radiation generating apparatus according to the present exemplary embodiment.

In present exemplary embodiment, a radiation generating apparatus 20 includes a radiation generation unit 18 having a radiation generation tube 1, and an objective unit 19 having a collimator 23.

With reference to FIG. 1A, the radiation generation unit 18 according to the present exemplary embodiment is described. The radiation generation unit 18 according to the present exemplary embodiment includes the radiation generation tube 1, and a storage container 16 for storing the radiation generation tube 1. The radiation generation unit 18 can further includes, in the inside 43 of the storage container 16, a drive circuit 15 for driving the radiation generation tube 1.

The drive circuit 15 can be provided outside of the storage container 16. The radiation generation unit 18 can further include an insulation fluid (not illustrated), in the inside 43 of the storage container 16, to accelerate heat dissipation of the radiation generation tube 1 or the drive circuit 15. The insulation fluid can be perfluoropolymer oil, silicone oil, or transformer oil.

For the storage container 16, as a material having high heat resistance and chemical stability, a metallic material such as stainless steel can be used. In terms of radiation performance of the radiation generation unit 18, a high-thermal-conductivity material such as copper can be suitably used. The storage container 16 can include a window 17 for efficiently extracting radiation 11 emitted from the radiation generation tube 1 to the outside of the radiation generation unit.

The window 17 can be made of a light element such as graphite. In terms of the thermal conductivity and heat resistance, aluminum, beryllium, diamond-like carbon, or diamond can be preferably used as the window 17 material.

The radiation generation tube 1 includes, in an inner space 13 of an envelope 6 in which the inside has been evacuated, at least an electron emitting source 3 having at least an electron emitting member 2. The radiation generation tube 1 includes the target 9 that receives emission of the electron beam 5 from the electron emitting member 2 and generates radiation.

The target 9 includes the target layer 42 containing a target material, and the base member 41 that supports the target layer 42. The target 9 is disposed in such a manner that the target layer 42 and the electron emitting source 3 face each other. The target layer 42 can include a target material made of a metal of an atomic number of 26 or greater such as silver, gold, tantalum, molybdenum, or tungsten. As the target material, an appropriate material can be selected in terms of heat resistance, and in consideration of a melting point and thermal conductivity.

Hereinafter, with reference to FIG. 1B and FIGS. 2A to 2D, a specific structure of the target 9 will be described. The target 9 illustrated in FIG. 1B shows a cross-sectional view (left diagram) of the target 9 in which the target 9 provided in the radiation generation tube 1 is enlarged, and a plan view of the target 9 taken along the line H-H' in the cross-section in the left diagram.

Figure 7A:
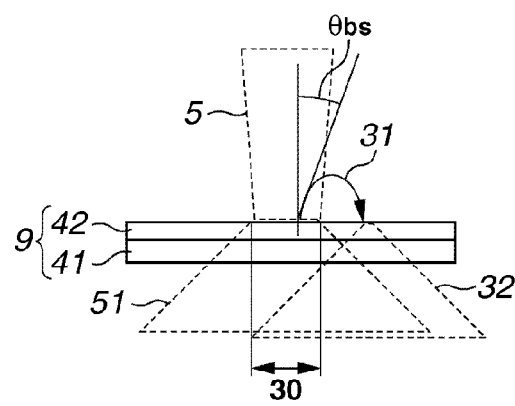
FIGS. 7A to 7D are schematic diagrams illustrating problems to be solved by the present invention.
Figure 7B:
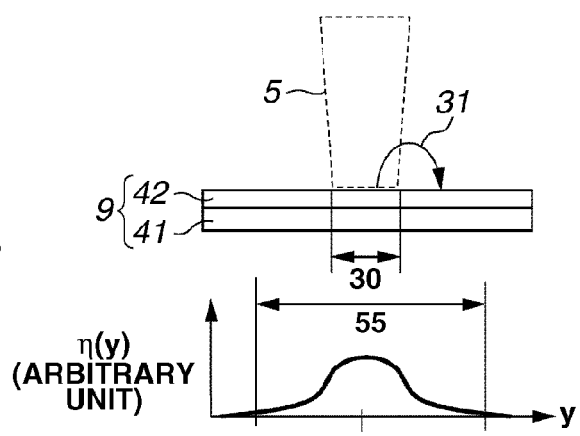

A periphery 62 of the target layer 42 has a portion separately located from a periphery 61 of the base member 41. Such an arrangement of the target layer 42 enables reduction in generation of "off-focal radiation due to re-entering radiation" described in FIG. 7B and "off-focal radiation due to re-entering reflected electrons" described in FIG. 7D.

To reduce at least the two types of off-focal radiation of "off-focal radiation due to re-entering radiation" and "off-focal radiation due to re-entering reflected electrons", it is preferable to match the size of the target layer 42 to the size of the focal spot of the electron beam. However, practically, in consideration of a distribution of the backscattering angle θbs of backscattering electrons 31, a suitable size of the target layer 42 is larger than the focal spot size of the electron beam, and smaller than the size of the base member 41. Further, in consideration of an alignment deviation to the target layer 42 of the electron beam 5 due to temperature change in an operating condition of the radiation generation apparatus, it is more preferable that the periphery 62 of the target layer 42 is formed in the range from the position 1.25 times of the focal diameter 30 to the position 0.8 times of the periphery 61. More preferably, the periphery 62 of the target layer 42 is formed in the range from the position 1.1 times of the focal diameter 30 to the position 0.9 times of the periphery 61.

Further, to prevent charging and electron-beam damage due to the direct electron incident of the electron beam 5 to the base member 41, it is preferable that the diameter of the target layer defined by the periphery of the target layer 42 is larger than the irradiation diameter 30 of the electron beam 5 to be formed on the target layer 42.

Figure 2A:
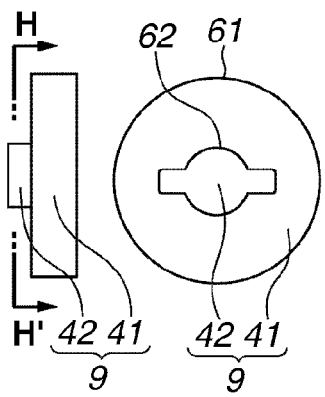
FIGS. 2A to 2D illustrate a target according to an exemplary embodiment of the present invention.
Figure 2B:
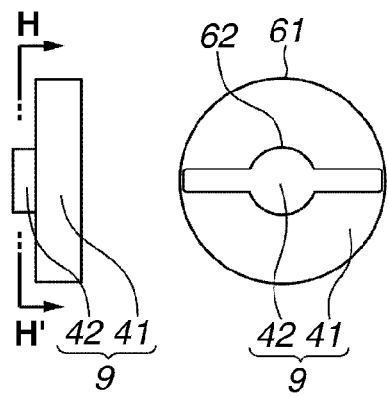

FIGS. 2A and 2B illustrate modifications of the target 9 illustrated in FIG. 1B. The targets 9 illustrated in FIGS. 2A and 2B differ from the target 9 illustrated in FIG. 1B in that the target layer 42 has portions locally extended from the periphery 62 toward the periphery 61. Both of the targets 9 illustrated in FIGS. 2A and 2B have, similar to the target 9 illustrated in FIG. 1B, a separated area between the periphery 61 of the base member and the periphery 62 separated from the periphery 61 of the base member.

In the above-mentioned separated area, a target material containing an element of a high atomic number is not disposed. Consequently, in the separated area, emission of electrons reflected from the area of the electron beam focal spot into the separated area does not cause generation of at least two types of off-focal radiation of "off-focal radiation due to re-entering radiation" and "off-focal radiation due to re-entering reflected electrons".

Figure 2C:
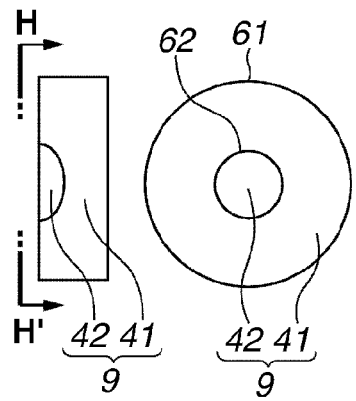

In the target layer 42 applicable to the radiation generating apparatus according to the present exemplary embodiment, it is not always necessary that the target layer 42 has a certain film thickness, but as in the target 9 illustrated in FIG. 2C, the film thickness of the target layer 42 can be reduced toward the periphery 62. Further, in the present exemplary embodiment, the target layer 42 is not limited to the target layer 42 formed on the surface of the base member 41, for example, the target layer 42 can be embedded in the base member 41 as illustrated in FIG. 2C. The target 9 like that illustrated in FIG. 2C can be formed, for example, according to an ion plating method or an electrochemical method by locally pushing a target material from one surface of the base member 41 into the base member 41.

Figure 2D:
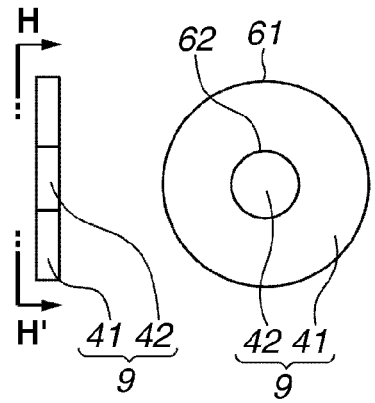

As a supporting method of the target layer 42 with the base member 41, as illustrated in FIG. 2D, at a position separated inwardly from the periphery 61 of the base member 41, the periphery 62 of the target layer 42 can be circularly supported in a diaphragm shape.

With reference to FIGS. 2E to 2J, a specific potential regulation structure of the target 9 will be described.

Figure 2E:
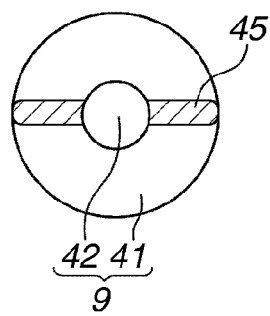
FIGS. 2E to 2J illustrate potential-regulating structures of the target according to an exemplary embodiment.
Figure 2F:
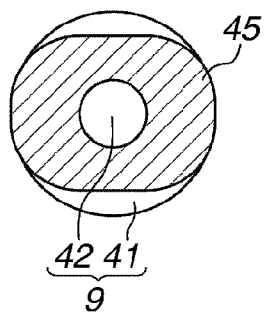
Figure 2G:
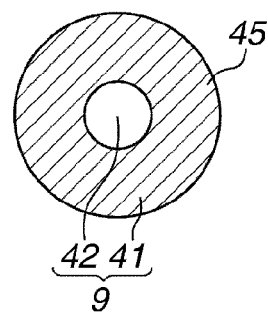
Figure 2H:
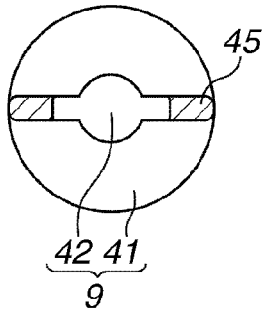
Figure 2I:
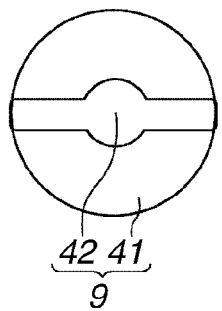

FIGS. 2E to 2G illustrate a potential regulation structure, which is not illustrated in the target 9 illustrated in FIG. 1B, as an electrode 45. The electrodes 45 in FIGS. 2E to 2G are formed to be sequentially arranged within areas from the periphery 61 of the base member 41 to the periphery 62 of the target layer 42.

The electrodes 45 in FIGS. 2E to 2G differ from each other in the formation areas of the electrodes 45 to the base member 41. The electrode 45 is provided only to regulate the potential of the target layer 42 to an anode potential. Consequently, the electrode 45 can be a conductive material made of a material having a lower atomic number than the atomic number of the target material contained in the target layer 42. For example, aluminum, chromium, titanium, or graphite can be used for the electrode 45.

The electrode 45 can be formed to have a film thickness for ensuring conductivity enough to regulate the potential as a lower limit, and a film thickness equal to or thinner than one-tenth of the film thickness of the target layer 42 as an upper limit to reduce the interaction with the incident electrons. For example, the film thickness can be between 1 nm to 1 μm. A film thickness of the electrode 45 between 10 nm to 100 nm enables both more stable potential regulation of the target layer 42 and reduction of the off-focal radiation.

As described above, by the arrangement of the electrode 45 formed of a material of a small atomic number and small thickness in the separated area to regulate the potential of the target layer 42 disposed to separate inwardly from the periphery of the base member 41, in the separated area, "off-focal radiation due to re-entering radiation" and "off-focal radiation due to re-entering reflected electrons" can be reduced.

Figure 2J:
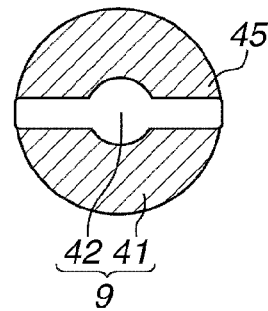

Similarly, FIG. 2J illustrates a relation of connection between the electrode 45, which is not illustrated in the target 9 illustrated in FIG. 2B, and the target layer 42. In the target 9 illustrated in FIG. 2(I), the extended portions of the target layer 42 reach the periphery 61 of the base member 41, and the extended portions can be used as a potential regulation structure of the target layer 42. In this structure, it is not necessary to separately provide an electrode.

The radiation generation tube 1 further includes the cylindrical backward shielding member 40 located at the electron emitting source side of the target 9 and having an electron incident opening 8. The backward shielding member 40 is disposed at the rear side of the target 9 for at least one purpose of the six purposes described below.

The first purpose of the backward shielding member 40 is to reduce electron damage and charging to the structural members of the radiation generation tube such as a cathode, a convergent electrode, and an insulation tube (not illustrated) located in the rearward position with respect to the target 9. The second purpose of the backward shielding member 40 is to reduce radiation damage and malfunction to the structural members of the radiation generation apparatus such as a drive circuit and cooling medium (not illustrated) located in the rearward position with respect to the target 9. The third purpose of the backward shielding member 40 is to accelerate heat radiation of the target 9, that is, to prevent overheating of the target 9. The fourth purpose of the backward shielding member 40 is to prevent radiation leakage to an ambient environment. The fifth purpose of the backward shielding member 40 is to reduce the weight of the radiation generating apparatus by disposing the backward shielding member at a position near a radiation generation area. The sixth purpose of the backward shielding member 40 is to increase an amount of radiation to be emitted toward the front of the target 9.

The backward shielding member 40 can be made of a material containing at least a metal of an atomic number of 26 or greater such as copper or iron. To reduce a radiation incident amount to other structures disposed posterior to the target 9, it is preferable that the backward shielding member 40 includes at least a metal of an atomic number of 42 or greater such as silver, gold, molybdenum, tantalum, or tungsten.

Further, the backward shielding member 40 includes at least the target material contained in the target layer 42, that is, in a case where the backward shielding member 40 includes a heavy metal material common to the target layer 42, the radiation due to the backward shielding member includes characteristic radiation due to the target layer 42, and thereby the intensity of the radiation to be emitted forward can be increased.

Figure 7C:
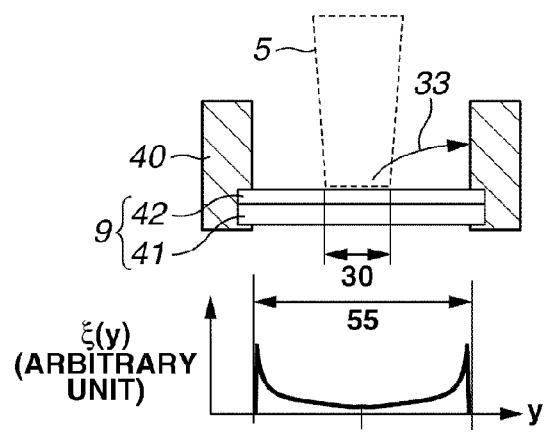

The action of increase in the intensity of the radiation to be emitted forward is specifically described. In FIG. 7C, in the radiation intensity distribution $\xi(y)$ of the radiation due to re-entering reflected electrons due to the backward shielding member 40, the radiation in the range overlapping with the focal diameter 30 is added to the intensity of the radiation 51 within focal spot in FIG. 7A, and thereby the radiation intensity can be obtained. In the radiation generating apparatus according to the present exemplary embodiment, the off-focal radiation to be emitted toward the front of the target from positions other than the focal diameter 30 can be reduced, and consequently, the user can optimize the use of the effect of the increase in the radiation within focal spot.

The potential of the target 9 according to the present exemplary embodiment is regulated to an anode potential that is higher about 20 kV to 200 kV than the potential of the electron emitting source 3. Further, the target 9 can be electrically connected to a high-tension circuit (not illustrated) via an anode member (not illustrated).

The backward shielding member 40 can also serve as an anode member 40, and in such a case, the target 9 can be electrically and mechanically connected to the backward shielding member 40 via a conductive joint material (not illustrated). As the conductive joint material, a brazing filler metal containing silver, tin, or copper as components can be used. The high-tension circuit can be provided in the drive circuit 15.

The radiation generation tube 1 according to the present exemplary embodiment includes the envelope 6 having a cathode provided with the electron emitting source 3, an anode provided with the target 9, and an insulating tube for electrically insulating the cathode and the anode. To the insulating tube, the cathode and the anode are fixed with a predetermined distance.

The pressure in the inner space 13 of the envelope 6 is reduced to vacuum to a degree electronic irradiation from the electron emitting source 3 to the target 9 can be performed. The pressure in the inner space 13 of the envelope 6 may be reduced to a degree enough to ensure a mean free path of the electron beam 5, and typically, to the range from $1 \times 10^{-8}$ Pa to $1 \times 10^{-4}$ Pa. To maintain the degree of vacuum, the radiation generation tube 1 can be provided with a getter (not illustrated) exposed in the inner space 13.

The electron emitting source 3 according to the present exemplary embodiment is connected to a drive circuit disposed outside of the radiation generation tube 1 via an electric current introduction terminal 4 to enable control of a radiation generation amount to be emitted from the radiation generation tube 1 from the outside of the radiation generation tube 1. The electric current introduction terminal 4 is electrically connected to the drive circuit 15, and further electrically connected to a grid electrode and a convergence electrode (not illustrated) provided to the electron emitting member 2 and the electron emitting source 3.

With reference to FIG. 1A, the objective unit 19 according to the present exemplary embodiment is described. The objective unit 19 according to the present exemplary embodiment includes the collimator 23 having movable diaphragms 56 and 57, an adjusting device 52 for varying the size of an opening 53 defined by the movable diaphragms 56 and 57, and the storage container 16 for storing the collimator 23 and the adjusting device 52.

The collimator 23 is disposed at the opposite side of the electron emitting source side of the target 9, that is, disposed anterior to the target 9. The collimator 23 shields at least a part of radiation 11 emitted toward the front of the target 9, and allows the rest of the radiation 11 to pass through via an opening 53 toward the front of the collimator 23. In other words, with the opening 53, the collimator 23 defines an angle for extracting the radiation 11 emitted from the target 9 toward the front of the target 9.

The objective unit 19 according to the present exemplary embodiment includes the adjusting device 52 being connected to the collimator 23, the adjusting device 52 for varying the opening diameter of the collimator 23. In the present exemplary embodiment, based on a higher-order instruction output from a higher-order instruction unit (not illustrated), or an operation instruction of an operator, the adjusting device 52 moves the movable blades 56 and 57 of the collimator 23 to vary the size of the opening of the collimator 23, that is, the opening diameter.

Figure 7D:
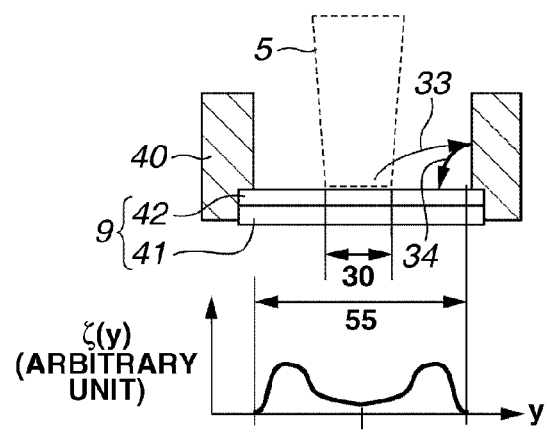

With reference to FIG. 1A and FIGS. 7C and 7D, off-focal radiation reduction action performed by the radiation generating apparatus having the collimator 23 according to the present exemplary embodiment of the present invention will be described.

When the radiation generating apparatus illustrated in FIG. 1A is operated, at least a part of backscattering electrons generated at the target layer 42 enters the backward shielding member 40. As a result, due to the backward shielding member 40, at least two types of off-focal radiation of "off-focal radiation due to backward shielding member" and "off-focal radiation due to re-entering reflected electrons" are emitted toward the front of the target 9. The at least two types of the off-focal radiation of "off-focal radiation due to backward shielding member" and "off-focal radiation due to re-entering reflected electrons" have local maximum values in the generation distribution $\xi(y)$ and $\zeta(y)$ beyond the focus area formed on the target 9 by the electron beam 5.

The collimator 23 performs the reduction action for each of the off-focal radiation generation distributions $\xi(y)$, and $\zeta(y)$ of the above-mentioned at least two types of "off-focal radiation due to backward shielding member" and "off-focal radiation due to re-entering reflected electrons".

In summary, the radiation generating apparatus 20 according to the present exemplary embodiment of the present invention has a first feature that the target layer 42 includes the part of the periphery 62 of the target layer 42 separated from the periphery 61 of the base member 41, and a second feature that the adjusting device 52 connected to the adjusting device 52 for varying the opening diameter of the opening 53 of the collimator 23 is provided. The radiation generating apparatus 20 according to the present exemplary embodiment of the present invention can, by the first feature, reduce at least "off-focal radiation due to re-entering radiation" and "off-focal radiation due to re-entering reflected electrons", and by the second feature, reduce at least "off-focal radiation due to backward shielding member" and "off-focal radiation due to re-entering reflected electrons".

Figure 3A:
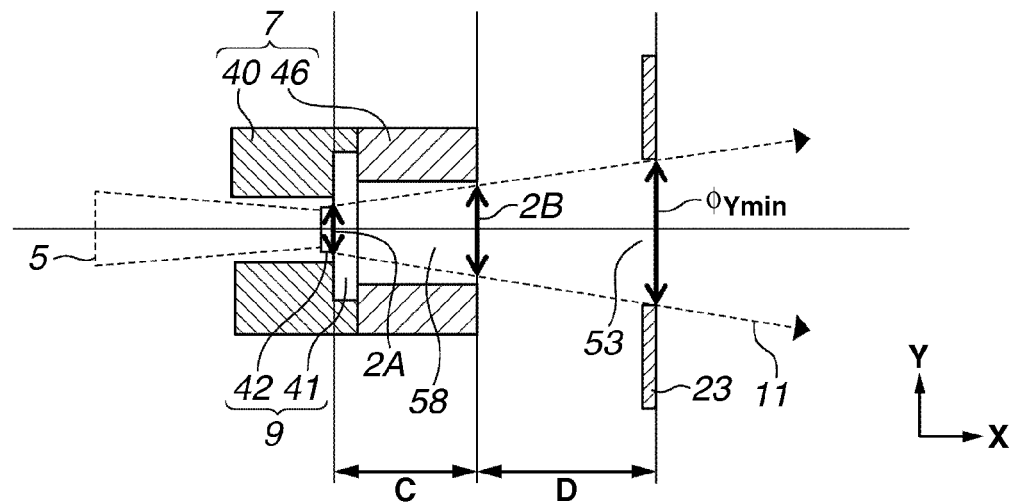
FIG. 3A illustrates an arrangement for giving a minimum diameter of the opening diameter of the collimator according to an exemplary embodiment.
Figure 3B:
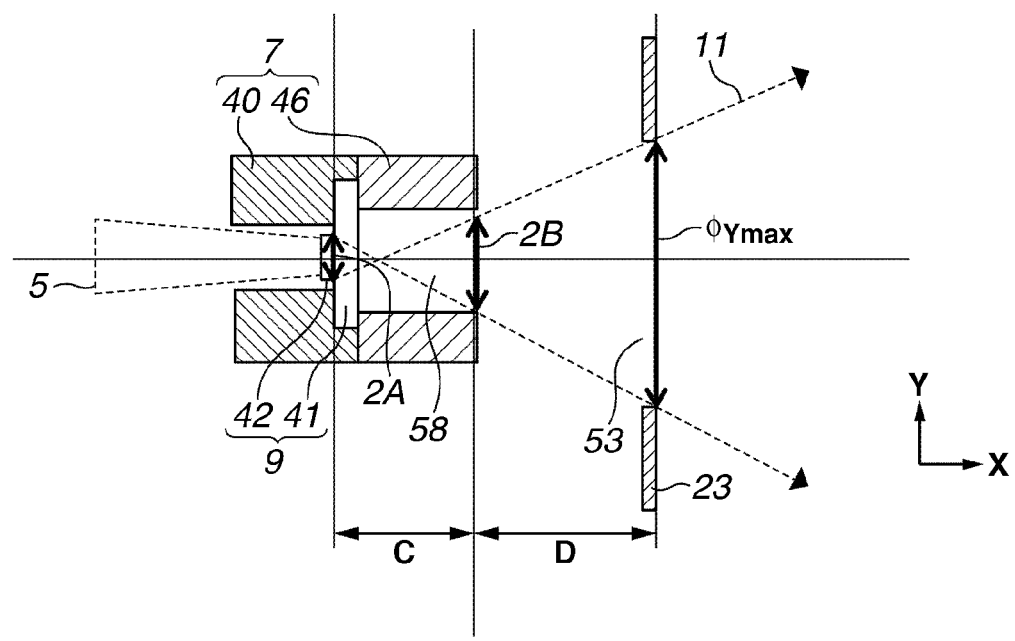
FIG. 3B illustrates an arrangement for giving a maximum diameter of the opening diameter of the collimator according to an exemplary embodiment.

With reference to FIGS. 3A and 3B, in an arrangement having a tubular forward shielding members 46 located in front of the target 9, a relationship in the arrangement of the collimator 23, the forward shielding members 46, and the target 9 for further increasing the effects of the action implemented by the second feature in the present exemplary embodiment of the present invention will be described.

FIG. 3A illustrates, in the radiation generating apparatus having the target 9, the forward shielding members 46, and the collimator 23, a condition $\Phi_{min}$ for an opening diameter for preventing reduction of the radiation within focal spot as much as possible while reducing the off-focal radiation. In other words, for the opening diameter $\Phi$ of the collimator 23, by including at least the $\Phi_{min}$ in a variable range of the opening diameter $\Phi$ of the opening 53, while reducing the off-focal radiation, the reduction in the radiation within focal spot can be prevented as much as possible.

Consequently, in the radiation generating apparatus according to the present exemplary embodiment, a condition for the opening diameter of the collimator 23 for preventing the reduction of the radiation within focal spot as much as possible while reducing the off-focal radiation is to satisfy the following general formula (1).

$$\Phi_{min} \leq 2A + 2 \times (B-A) \times (C+D)/C, \Phi \geq \Phi_{min} \qquad \text{formula (1)},$$

where 2A is an electron beam irradiation diameter to be formed on the target layer, 2B is a tube outgoing diameter, C is a distance between a virtual plane for defining an inner diameter of a tube outgoing opening 58 and the target layer, and D is a distance between a virtual plane for defining an opening diameter of the collimator, and the virtual plane for defining the inner diameter of the tube outgoing opening 58.

On the other hand, FIG. 3B illustrates, in the radiation generating apparatus having the target 9, the forward shielding members 46, and the collimator 23, a condition $\Phi_{max}$ for an opening diameter for substantially eliminating reduction of the radiation within focal spot due to the collimator 23 while reducing the off-focal radiation to a minimum. In other words, for the opening diameter $\Phi$ of the collimator 23, by including at least the $\Phi_{max}$ in the variable range of the opening diameter $\Phi$ of the opening 53, while reducing the off-focal radiation to a minimum, the reduction in the radiation within focal spot due to the collimator 23 can be eliminated.

Consequently, in the radiation generating apparatus according to the present exemplary embodiment, a condition for the opening diameter of the collimator 23 for substantially eliminating the reduction of the radiation within focal spot due to the collimator 23 while reducing the off-focal radiation to a minimum is to satisfy the following general formula (2).

$$\Phi_{max} \geq -2B + 2 \times (A+B) \times (C+D)/C, \Phi \leq \Phi_{max} \qquad \text{formula (2)}$$

In FIGS. 3A and 3B, for the description of the conditions in the Y direction of the opening 53, the Y-X planes are representatively described. In a case of the collimator 23 having the opening 53 of a shape other than the circular shape having an anisotropy, in a plurality of directions i (i=0, 1, 2 . . . ) for representatively defining an opening diameter, to each of, or a part of the directions i, the general formula (1) or the general formula (2) can be applied.

With reference to FIGS. 4A to 4F, modifications of a shielding member 7 to be applied to the radiation generating apparatus according to the present exemplary embodiment of the present invention, the target-forward shielding member distance C, the inner diameter 2B to be defined by the tube outgoing opening 58 of the forward shielding member, and the electron beam irradiation diameter 2A will be described.

FIGS. 4D to 4F illustrate the target 9 and the peripheral structure of the target 9 in which the tubular forward shielding member 46 is disposed anterior to the target 9 and posterior to the collimator 23.

The tubular forward shielding member 46 according to the present exemplary embodiment shields, from the radiation generated at the target layer 42, at least a part of the radiation 11 emitted toward the front of the target 9, and allows the rest of the radiation 11 to pass through via the opening 58 toward the front.

In the present exemplary embodiment, the target-forward shielding member distance C is determined by a distance between a virtual plane IF for defining an inner diameter of the tube outgoing opening 58 of the forward shielding member 46, and an interface between the target layer 42 and the base member 41.

The virtual plane IF according to the present exemplary embodiment is determined as follows. First, the point on the target layer 42 where the perpendicular line virtually extended from the center of the focal diameter of the electron beam 5 that is direct incident electrons to the interface IT between the target layer 42 and the base member 41 intersects with the interface IT is determined to be a reference point. The reference point is the center of the electron irradiation region of the target 9. Next, a geometrical condition for a virtual conical surface SC to contact the forward shielding member 46 is to be defined. The virtual conical surface SC is a conical surface of a virtual cone having the reference point as a vertex and a viewing angle from the reference point toward the opening of the tubular forward shielding member 46 as a spray cone angle, the virtual conical surface SC extending in a direction increasing a distance from the target 9. Then, within the range the virtual conical surface SC contacts the forward shielding member 46, a virtual plane including a region farthest from the target 9 is defined as IF.

A distance between the defined IF and the interface between the target layer 42 and the base member 41 is the target-forward shielding member distance C.

Further, the bottom surface of the cone formed by the defined IF and the virtual conical surface SC is defines as the tube outgoing opening 58, and the inner diameter of the tube outgoing opening 58 is determined to be the tube outgoing opening diameter 2B. In a case where the bottom surface is a circle, the diameter of the bottom surface is to be 2B, and in a case where the bottom surface is an ellipse, 2B has a length distribution from the minor axis to the major axis, and in such a case, the minor axis and the major axis can be used as representative values of the outgoing opening diameter 2B. In a case of a forward shielding member shape forming a cone having a bottom surface of a polygonal shape, inner diameters of the outgoing opening corresponding to a minimum angle and a maximum angle of the vertical angles of the cone respectively can be used as representative values of a minimum value and a maximum value of the outgoing opening diameter 2B.

With reference to FIGS. 5A to 5E, the collimator applicable to the radiation generating apparatus according to the present exemplary embodiment of the present invention will be described. FIG. 5A is a plan view illustrating the collimator 23 illustrated in FIG. 1C viewed from the back, that is, from the target 9 direction. FIGS. 5B to 5E are cross-sectional views of the collimator 23 taken along the guide lines K-K', L-L', M-M', and N-N' in FIG. 5A.

The collimator 23 may have a density and a thickness enough to shield the radiation emitted from the target 9 illustrated in FIG. 1A, and for the collimator 23, a metallic material can be used. To further reduce the size of the radiation generating apparatus, the movable diaphragms 56 and 57 can contain a heavy metal such as zirconium, molybdenum, tantalum, or tungsten to reduce the thickness of the collimator 23 in the optical axis direction.

As illustrated in FIG. 1A, in a case where a matrix shaped collimator 23 is formed with a plurality of the movable diaphragms 56 and 57, each movable blade has a finite thickness, and consequently, both of the above-described target-collimator distance C+D, and the forward shielding member-collimator distance D can have a distribution in the circumferential direction surrounding the opening 53 viewed from the center portion of the opening 53. For example, as illustrated in FIG. 5A, in a case where the collimator 23 has a matrix shape forming the rectangle opening 53, an opening diameter $\Phi_Z$ in the Z direction illustrated in FIG. 5E is defined by a pair of the movable blades 57, and an opening diameter $\Phi_Y$ in the Y direction illustrated in FIG. 5C is defined by a pair of the movable blades 56.

In the present exemplary embodiment, a virtual plane PZ defining the opening diameter $\Phi_Z$ in the Z direction is separated from the collimator 23 or the forward shielding member by a thickness t of the movable blade 56 in the X direction as compared to a virtual plane PY defining the opening diameter $\Phi_Y$ in the Y direction. In the present exemplary embodiment, to prevent the off-focal radiation from emitting to the radiation detector 27 side, it is preferable that $\Phi_Z$ satisfies the above-mentioned general formula (1), and the $\Phi_Y$ satisfies the general formula (2).

In other words, it is preferable that the following general formulas (3) and (4) are satisfied, and further the general formula (5) is satisfied to obtain a high passage rate of the radiation within focal spot spreading in the Y direction of the opening 53 at the opening 53.

$$\Phi_Z \leq \Phi_Y \quad \text{formula (3)},$$

$$\Phi_{Zmin} \leq 2A+2\times(B-A)\times(C+D_{PZ})/C, \Phi_Z \geq \Phi_{Zmin} \quad \text{formula (4)},$$

$$\Phi_{Ymax} \leq -2B+2\times(A+B)\times(C+D_{PY})/C, \Phi_Y \leq \Phi_{Ymax} \quad \text{formula (5)},$$

where $\Phi_{Zmin}$ is a minimum value in the variable range of the opening 53 in the Z direction, $\Phi_{Ymax}$ is a maximum value in the variable range of the opening 53 in the Y direction, $D_{PZ}$ is a distance between the forward shielding member and a virtual plane PZ defining the opening diameter $\Phi_Z$ of the collimator 23, and $D_{PY}$ is a distance for defining the opening diameter $\Phi_Y$ of the collimator 23.

With respect to a condition satisfying the general formulas (3) and (4), in other words, in a case where the opening 53 of the collimator has a rectangular opening shape having a one side of a length P, and the other side of a length Q, a minimum value of the opening diameter to be defined by the mechanism for varying the opening diameter of the opening 53 corresponds to a minimum value of the length of P or Q not longer than the other one.

Similarly, with respect to a condition further satisfying the general formula (5), in other words, in a case where the opening 53 of the collimator has a rectangular opening shape having a one side of a length P, and the other side of a length Q, a maximum value of the opening diameter to be defined by the mechanism for varying the opening diameter of the opening 53 corresponds to a maximum value of the length of P or Q not shorter than the other one.

Further, in the present exemplary embodiment, to prevent the off-focal radiation spreading in the Y direction of the opening 53 from emitting to the radiation detector 27 side, it is more preferable to satisfy the following general formula (6), and to obtain a high passage rate of the radiation within focal spot spreading in the Z direction of the opening 53 at the opening 53, it is more preferable to satisfy the general formula (7).

$$\Phi_{Ymin} \leq 2A+2\times(B-A)\times(C+D_{PY})/C, \Phi_Y \geq \Phi_{Ymin} \quad \text{formula (6)},$$

$$\Phi_{Zmax} \geq -2B+2\times(A+B)\times(C+D_{PZ})/C, \Phi_Z \leq \Phi_{Zmax} \quad \text{formula (7)},$$

where, $\Phi_{Ymin}$ is a minimum value in the variable range of the opening 53 in the Y direction, and $\Phi_{Zmax}$ is a maximum value in the variable range of the opening 53 in the Z direction.

As in the present exemplary embodiment, in the collimator defining different opening diameters in different directions at positions of different distances from the target, as described in the present exemplary embodiment, to reduce the off-focal radiation, it is preferable to arrange the movable blades 57 defining a larger opening diameter $\Phi_Y$ closer to the target as compared to the movable blades 56 defining a smaller opening diameter $\Phi_Z$.

The collimator 23 applicable to the present exemplary embodiment of the present invention is not limited to the above-described matrix shape forming the rectangular opening 53. Alternatively, modifications include, for example, the collimator 23 of an iris diaphragm shape (not illustrated) formed by radially arranging a plurality of diaphragm blades to form a substantially circular opening, and the collimator 23 formed by arranging diaphragm blades in a separated state in an optical axis direction.

Figure 6A:
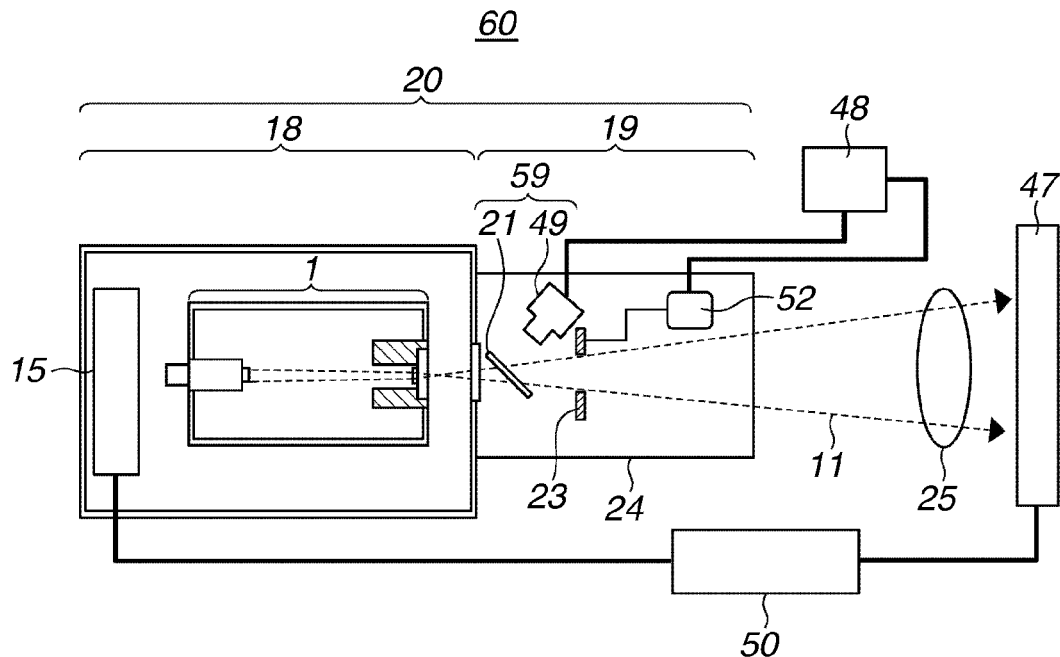
FIG. 6A illustrates a radiation imaging apparatus having a radiation detector and an optical camera according to an exemplary embodiment.
Figure 6B:
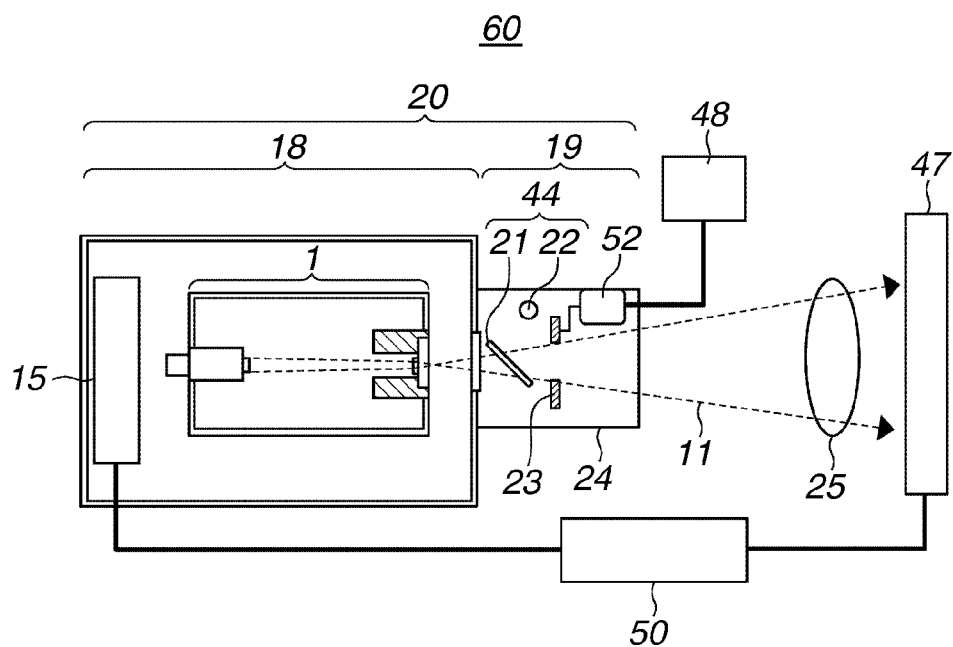
FIG. 6B illustrates a radiation imaging apparatus having a radiation detector and a sighting optical system.

With reference to FIGS. 6A and 6B, as another exemplary embodiment of the present invention, a radiation imaging apparatus having a radiation generating apparatus according to an exemplary embodiment of the present invention and a radiation detector will be described. FIG. 6A illustrates an exemplary embodiment of a radiation imaging apparatus 60 having an imaging field acquisition unit 59 disposed to provide an image acquisition area in the direction to face a radiation detector 47. FIG. 6B illustrates a modification of the radiation imaging apparatus 60 having a sighting optical system 44 for providing an exposure field.

With reference to FIG. 6A, an exemplary embodiment including the adjusting device 52 for varying an opening diameter of the collimator 23 and the imaging field acquisition unit 59 will be described. In the present exemplary embodiment, the imaging field acquisition unit 59 includes a mirror 21 disposed in a tilted state to the emission center axis of the radiation 11, and an optical camera 49 having an imaging field toward the mirror 21. In such an arrangement, the optical camera 49 can define the imaging field toward the radiation detector 47. To align the imaging field and the exposure field, it is preferable that the position of the optical camera 49 to the mirror 21 is a conjugate position to the focal spot on the target.

The adjusting device 52 for varying the opening diameter of the collimator 23 is connected to the optical camera 49 via an opening diameter instruction unit 48. The present exemplary embodiment of the present invention includes an arrangement in which the imaging field acquisition unit 59 is disposed outside of an objective lens barrel 24.

In the present exemplary embodiment, based on an acquired image acquired by the optical camera 49, the imaging field acquisition unit 59 determines a detection range of the radiation detector 47 or a size of a region of interest of a test object 25. Then, based on the detection range of the radiation detector 47 or the size of the region of interest of the test object 25, the imaging field acquisition unit 59 can send information including the size of the exposure field to the opening diameter instruction unit 48. The opening diameter instruction unit 48, based on the received information including the size of the exposure field, sends an instruction signal for specifying the opening diameter of the collimator 23 to the adjusting device 52.

More specifically, a method for determining a size of the exposure field by the opening diameter instruction unit 48 is described. In the present exemplary embodiment, before a timing of determining an exposure field, the opening diameter instruction unit 48, in advance, issues an instruction to the adjusting device 52 to fully open the opening of the collimator 23. By performing the step of fully opening the opening of the collimator 23, information including a virtual exposure field corresponding to an area wider than a region of interest can be sent to the opening diameter instruction unit 48.

Then, the opening diameter instruction unit 48 provides the virtual exposure field to an operator (not illustrated) on a display screen (not illustrated). The operator, from the provided virtual exposure field, acquires the information including the exposure field corresponding to the region of interest by an input unit (not illustrated), and sends the acquired exposure field information to the opening diameter instruction unit 48.

The opening 53 of the collimator 23 at the timing of acquiring the virtual exposure field with the optical camera 49 is not limited to the fully open condition, and an opening of a size including the region of interest of the subject 25, and the size enough to acquire a region wider than the region of interest is to be ensured. The image to be acquired by the optical camera 49 can be a visible light image or an image acquired using other wave lengths such as an infrared light image.

With reference to FIG. 6B, an exemplary embodiment including the adjusting device 52 for varying an opening diameter of the collimator 23 and the sighting optical system 44 will be described. In FIG. 6B, similarly to the present exemplary embodiment illustrated in FIG. 6A, the adjusting device 52 for varying an opening diameter of the collimator 23 is connected to the opening diameter instruction unit 48.

In the present exemplary embodiment, the sighting optical system 44 includes the mirror 21 disposed in a tilted state to the emission center axis of the radiation 11, and a light source 22 having an emission direction toward the mirror 21.

The emission wavelength of the light source 22 is not limited to visible light, and ultraviolet light can be used. As the light source 22, it is preferable to employ a visible light source to directly provide an exposure range to a subject or an operator.

In the present exemplary embodiment, the objective unit 19 can include the objective lens barrel 24 for storing at least the mirror 21 and the light source 22.

To ensure an illuminance contrast of an area to which exposure is provided with respect to an area where the exposure is not provided, it is preferable to make the objective lens barrel 24 with an opaque member to the wavelength of the light provided by the objective unit. Further, to ensure an illuminance contrast of an area where exposure is provided with respect to an area where the exposure is not provided, it is preferable to provide, to the inner surface of the objective lens barrel 24, a member having a low reflectivity to the wavelength of the light provided by the objective unit to reduce diffused reflection.

In the present exemplary embodiment, based on recognition of an operator (not illustrated) by visual observation on an exposure range provided by the sighting optical system 44 in the direction toward the radiation detector 47, the operator can output an instruction signal instructing an opening diameter of the collimator 23 to the opening diameter instruction unit 48.

In the present exemplary embodiment, the opening diameter instruction unit 48, based on the detected region of the radiation detector 47, or the size of the interest region of the subject, sends an instruction signal for specifying the opening diameter of the collimator 23 to the adjusting device 52.

As a modification of the present exemplary embodiment illustrated in FIGS. 6A and 6B, a sensor (not illustrated) further provided to the radiation detector 47 can specify the size of the exposure range or the subject 25. For example, to the opening diameter instruction unit 48, information about a size of an exposure range or a subject can be sent via a detector control circuit 50 to control the opening of the collimator 23.

The above-mentioned sensor can be an optical sensor having a light-receiving sensitivity to the irradiation wavelength of the irradiation light source, or can be a piezoelectric sensor or a temperature sensor to determine a size of a subject. In the present exemplary embodiment, it is not limited to dispose the sensor (not illustrated) in the radiation detector 47, but the sensor can be disposed between the subject and the radiation generating apparatus 20, or before or after the radiation detector 47 with respect to the irradiation direction of the radiation 11.

The radiation generating apparatus according to the above-described exemplary embodiments of the present invention has the transmission type target and the backward shielding member, and consequently, in addition to the advantages of high output, small and lightweight, battery-powered, and portability, the following effects can be further provided.

The radiation generating apparatuses according to the above-described exemplary embodiments of the present invention can reduce effective focal spot increase due to backscattering reflected electrons at a target. This enables prevention of decrease in the resolution of an acquired image in applications of the radiation generating apparatuses according to the present exemplary embodiments of the present invention to radiation imaging apparatuses for medical diagnosis, and industrial non-destructive tests. As a result, radiation diagnosis at high resolutions can be performed. Consequently, according to the present exemplary embodiments of the present invention, the radiation generating apparatuses and radiation imaging apparatuses provided with high-power radiation emission and small and lightweight properties, and implementing high-resolution radiation image acquisition can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-187615 filed Aug. 28, 2012, which is hereby incorporated by reference herein in its entirety.

What is claimed is:

1. An X-ray generating apparatus comprising:
   an X-ray generating tube including:
      a cathode including an electron emitting source having an electron emitting member,
      an anode comprising:
         a target having a target layer receiving an electron beam emitted from the electron emitting source and generating an X-ray, and a support member supporting the target layer and transmitting the X-ray,
         wherein the electron emitting source and the target layer are disposed to face each other, and
      a tubular backward shielding member having a connection portion connected to the periphery of the support member and protruded from the connection portion toward the electron emitting source;
   a collimator having a plurality of movable blades which form an opening for defining an angle for extracting the X-ray at the opposite side of the electron emitting source side of the target; and
   an adjusting device connected to the plurality of movable blades, and configured to vary an opening diameter of the opening,
   wherein the target layer is distant from the connection portion via a separate portion so as to reduce an off-focal radiation due to re-entering electrons to the target layer from the tubular backward shielding member or the target layer, and
   wherein the collimator is configured to be controlled by the adjusting device so as to reduce an off-focal radiation due to the tubular backward shielding member and the separate portion.

2. The X-ray generating apparatus according to claim 1, wherein the separate portion is located annularly around the target layer.

3. The X-ray generating apparatus according to claim 1, wherein the target layer includes at least a target material made of a metal of an atomic number of 42 or greater, and the backward shielding member includes the target material.

4. The X-ray generating apparatus according to claim 1, wherein, between the periphery of the target layer and the periphery of the support member, the target has a region at which the support member is exposed in the separate portion.

5. The X-ray generating apparatus according to claim 1, wherein the target has an electrode formed to be sequentially arranged within an area from the periphery of the target layer to the periphery of the support member, and the electrode is made of a material having a lower atomic number than the atomic number of the target material.

6. The X-ray generating apparatus according to claim 5, wherein the target is electrically connected to the backward shielding member via the electrode.

7. The X-ray generating apparatus according to claim 1, wherein a diameter of the target layer defined by the periphery of the target layer is larger than an irradiation diameter of the electron beam to be formed on the target layer.

8. The X-ray generating apparatus according to claim 7, wherein the X-ray generating tube includes a forward shielding member which has a tube outgoing opening for allowing a part of the X-ray emitted from the target toward the front of the target to pass through and located between the target and the collimator, and the inner diameter of the tube outgoing opening is larger than the irradiation diameter.

9. The X-ray generating apparatus according to claim 8, wherein a minimum value of an opening diameter of the collimator is at least equal to or less than $2A+2\times(B-A)\times(C+D)/C$, where 2A is a diameter of an electron beam irradiated on the target layer, 2B is a tube outgoing diameter, C is a distance between a virtual plane for defining an inner diameter of the tube outgoing opening and the target layer, and D is a distance between a virtual plane for defining an opening diameter of the collimator, and the virtual plane for defining the inner diameter of the tube outgoing opening.

10. The X-ray generating apparatus according to claim 8, wherein a maximum value of an opening diameter of the collimator is at least equal to or less than $-2B+2\times(A+B)\times(C+D)/C$, where 2A is a diameter of an electron beam irradiated on the target layer, 2B is a tube outgoing diameter, C is a distance between a virtual plane for defining an inner diameter of the tube outgoing opening and the target layer, and D is a distance between a virtual plane for defining an opening diameter of the collimator, and the virtual plane for defining the inner diameter of the tube outgoing opening.

11. The X-ray generating apparatus according to claim 9, wherein the opening has a rectangular opening shape having one side of a length P, and the other side of a length Q, a minimum value of the opening diameter to be defined by the mechanism for varying the opening diameter of the opening corresponds to a minimum value of the length of P or Q not longer than the other one.

12. The X-ray generating apparatus according to claim 10, wherein the opening has a rectangular opening shape having one side of a length P, and the other side of a length Q, a maximum value of the opening diameter to be defined by the mechanism for varying the opening diameter of the opening corresponds to a maximum value of the length of P or Q not shorter than the other one.

13. The X-ray generating apparatus according to claim 1, wherein, among the movable blades, a movable blade configured to define a larger opening diameter is to be located at a position closer to the target as compared to movable blades defining a smaller opening diameter.

14. A radiograph system comprising:
   the X-ray generating apparatus according to claim 1, and
   an X-ray detector configured to detect an X-ray emitted from the X-ray generating apparatus and transmitted through a subject.

15. The radiography system according to claim 14, further comprising:
   an opening diameter instruction unit connected to the adjusting device, and configured to instruct an opening diameter determined based on a size of an exposure field to the adjusting device.

16. The radiography system according to claim 15, further comprising:
   an imaging field acquisition unit having an optical camera configured to define an imaging field toward the X-ray detector, and configured to determine a size of the exposure field based on an image acquired by the optical camera, and send the size of the exposure field to the opening diameter instruction unit.

17. The radiography system according to claim 15, further comprising:
   a sighting optical system located between a forward shielding member and the collimator, and configured to provide a virtual exposure field to an operator or a subject, and send the size of the exposure field determined based on the virtual exposure field to the opening diameter instruction unit.

18. The radiography system according to claim 17, wherein the sighting optical system includes at least a mirror configured to transmit the X-ray and reflect visible light, and a visible light source configured to emit visible light to the mirror.

19. The X-ray generating apparatus according to claim 1, wherein the tubular backward shielding member is protruded backwardly from the connection portion along a tube axis.

* * * * *